(12) United States Patent
Guzman

(10) Patent No.: US 8,211,091 B2
(45) Date of Patent: Jul. 3, 2012

(54) METHOD AND APPARATUS FOR CHARGING PUMP WITH LOCAL ANESTHETIC

(76) Inventor: Michael F. Guzman, Fortville, IN (US)

( * ) Notice: Subject to any disclaimer, the term of this patent is extended or adjusted under 35 U.S.C. 154(b) by 0 days.

(21) Appl. No.: 11/946,989

(22) Filed: Nov. 29, 2007

(65) Prior Publication Data
US 2009/0143731 A1 Jun. 4, 2009

(51) Int. Cl.
*A61K 9/22* (2006.01)
*A61M 3/00* (2006.01)
*A61N 5/00* (2006.01)

(52) U.S. Cl. ........... 604/890.1; 604/407; 141/18; 600/4; 600/5

(58) Field of Classification Search ............... 604/407, 604/403, 28, 512, 890.1; 141/18, 21, 27, 141/391; 600/4, 5
See application file for complete search history.

(56) References Cited

U.S. PATENT DOCUMENTS

| | | |
|---|---|---|
| 5,569,208 A | 10/1996 | Woelpper et al. |
| RE38,074 E | 4/2003 | Recinella et al. |
| 7,232,428 B1 | 6/2007 | Inukai et al. |
| 2002/0019608 A1 | 2/2002 | Mason et al. |
| 2002/0143294 A1 | 10/2002 | Duchon et al. |
| 2003/0004463 A1* | 1/2003 | Reilly et al. ............ 604/124 |
| 2003/0060704 A1 | 3/2003 | Emig et al. |

FOREIGN PATENT DOCUMENTS
WO 02/98493 A1 12/2002

OTHER PUBLICATIONS

International search report dated Apr. 21, 2009 from related PCT/US2008/084501, May 8, 2009.
http://www.bbraunusa.com/index.cfm?uuid=4E76A7DDD0B759A1E3602055BF3F9F8F.

* cited by examiner

*Primary Examiner* — Jackie Ho
*Assistant Examiner* — Leah Stohr
(74) *Attorney, Agent, or Firm* — Barnes & Thornburg LLP

(57) ABSTRACT

A kit for charging an infusion pump having a reservoir for holding a local anesthetic. The kit includes a first stopcock having an input port, a first input/output port and a second output port and a manual control for selectively coupling either the first input/output port or the second output port to the input port. The kit further includes a second stopcock having an input port, first and second output ports and a manual control for selectively coupling either the first output port or the second output port to the input port. The second output port of the first stopcock is adapted for coupling to the input port of the second stopcock. The kit further includes a syringe adapted to be coupled to the first input/output port of the first stopcock and tubing for coupling the input port of the first stopcock to a source of the liquid and for coupling the output port of the second stopcock to an input port of the pump.

11 Claims, 1 Drawing Sheet

METHOD AND APPARATUS FOR CHARGING PUMP WITH LOCAL ANESTHETIC

FIELD OF THE INVENTION

This invention relates to medical devices. It is disclosed in the context of certain self-contained pumps for the timed administration of local anesthetics, but it is believed to have other applications as well.

BACKGROUND OF THE INVENTION

Considerable effort has been directed over the past several years at reducing the trauma associated with certain surgical procedures and the recuperation times of patients on whom such surgeries are performed. Among these are, for example, knee replacement, knee reconstruction, shoulder reconstruction, and so on. In some cases, these patients are accident victims. In others, they simply suffer deterioration of the joint being reconstructed or replaced. In any case, more and more of these surgeries are being performed under local, rather than general, anesthetic. The local anesthetic then continues to be administered during the recuperation of the patient for pain management purposes.

There are several benefits associated with such a strategy. For example, the local anesthetics typically used in these cases also have antiseptic attributes owing to their maintenance of pHs in the surgical field that inhibit or retard bacterial growth.

Further, the morbidity/mortality complications associated with administration of general anesthetics are generally avoided by use of local anesthetics in these settings. The locally anesthetized patient typically remains conscious throughout the surgery.

Use of a general anesthetic requires the patient first to regain consciousness. Recovery can be promoted in orthopedic surgical cases, for example, by encouraging the patient to begin exercising the affected joint sooner after completion of the surgery, rather than later. Typically, the locally anesthetized patient can begin exercising the affected joint much sooner after completion of surgery.

DISCLOSURE OF THE INVENTION

According to an aspect of the invention, a kit is provided for charging an infusion pump having a reservoir for holding a liquid which is to be dispensed by the pump. The pump has an input port through which the reservoir is filled and an output port through which liquid in the reservoir is pumped by the pump. The kit includes a dual stopcock having an input port, an input/output port and two output ports, and first and second manual controls for controlling flow among the input port, the input/output port and the two output ports.

Illustratively, the kit further includes a syringe adapted to be coupled to the input/output port.

Illustratively, the kit further includes tubing for coupling the input port of the dual stopcock to a source of the liquid.

Illustratively, the kit further includes tubing for coupling one of the output ports of the dual stopcock to the input port of the pump.

According to another aspect of the invention, a kit is provided for charging an infusion pump having a reservoir for holding a liquid which is to be dispensed by the pump. The pump has an input port through which the reservoir is filled and an output port through which liquid in the reservoir is pumped by the pump. The kit includes a first stopcock having an input port, a first input/output port and a second output port and a manual control for selectively coupling either the first input/output port or the second output port to the input port. The kit further includes a second stopcock having an input port, first and second output ports and a manual control for selectively coupling either the first output port or the second output port to the input port, the second output port of the first stopcock adapted for coupling to the input port of the second stopcock.

Illustratively, the kit further includes a syringe adapted to be coupled to the first input/output port of the first stopcock.

Illustratively, the kit further includes tubing for coupling the input port of the first stopcock to a source of the liquid.

Illustratively, the kit further includes tubing for coupling the output port of the second stopcock to the input port of the pump.

Illustratively, the first and second stopcocks are provided in a common body.

According to another aspect of the invention, a method is provided for filling an infusion pump having a reservoir for holding a liquid which is to be dispensed by the pump. The pump has an input port through which the reservoir is filled and an output port through which liquid in the reservoir is pumped by the pump. The method comprises coupling a source of the liquid which is to be dispensed by the pump to an input port of a dual stopcock also having an input/output port, a first output port and a second output port, coupling the first output port of the dual stopcock to the input port of the pump, coupling a syringe to the input/output port of the dual stopcock, drawing from the source into the syringe an amount of liquid to be transferred to the pump, operating the stopcock to couple the syringe to the input port of the pump, and operating the syringe to transfer liquid from the syringe to the pump.

Illustratively, the method further comprises repeatedly drawing from the source into the syringe an amount of liquid to be transferred to the pump, operating the stopcock to couple the syringe to the input port of the pump, and operating the syringe to transfer liquid from the syringe to the pump until a desired amount of the liquid has been transferred to the pump.

Illustratively, the method further comprises drawing air into the syringe as the liquid is drawn into the syringe, operating the dual stopcock to couple the syringe to the second output port of the dual stopcock, orienting the syringe so that the air captured in the syringe can be expelled from the syringe substantially without expelling any of the liquid, and operating the syringe and the dual stopcock to expel air from the syringe through the second output port of the stopcock.

According to another aspect of the invention, a method is provided for filling an infusion pump having a reservoir for holding a liquid which is to be dispensed by the pump. The pump has an input port through which the reservoir is filled and an output port through which liquid in the reservoir is pumped by the pump. The method comprises coupling a source of the liquid which is to be dispensed by the pump to an input port of a first stopcock also having a first input/output port and a second output port, coupling the second output port of the first stopcock to an input port of a second stopcock having first and second output ports, coupling the first output port of the second stopcock to the input port of the pump, coupling a syringe to the first input/output port of the first stopcock, operating the first stopcock to couple the input port of the first stopcock to the first input/output port of the first stopcock, drawing from the source into the syringe an amount of liquid to be transferred to the pump, operating the first and second stopcocks to couple the syringe to the input port of the pump, and operating the syringe to transfer liquid from the syringe to the pump.

Illustratively, the method further comprises repeatedly drawing from the source into the syringe an amount of liquid to be transferred to the pump, operating the first and second stopcocks to couple the syringe to the input port of the pump, and operating the syringe to transfer liquid from the syringe to the pump until a desired amount of the liquid has been transferred to the pump.

Illustratively, the method further comprises drawing air into the syringe as the liquid is drawn into the syringe, operating the second stopcock to couple the syringe to the second output port of the second stopcock, orienting the syringe so that the air captured in the syringe can be expelled from the syringe substantially without expelling any of the liquid, and operating the syringe and the first and second stopcocks to expel air from the syringe through the second output port of the second stopcock.

Illustratively, the method further comprises providing the first and second stopcocks in a common body.

BRIEF DESCRIPTION OF THE DRAWINGS

The invention may best be understood by referring to the following detailed description and accompanying drawings which illustrate the invention. In the drawings.

DETAILED DESCRIPTION OF ILLUSTRATIVE EMBODIMENTS

Figure 1:
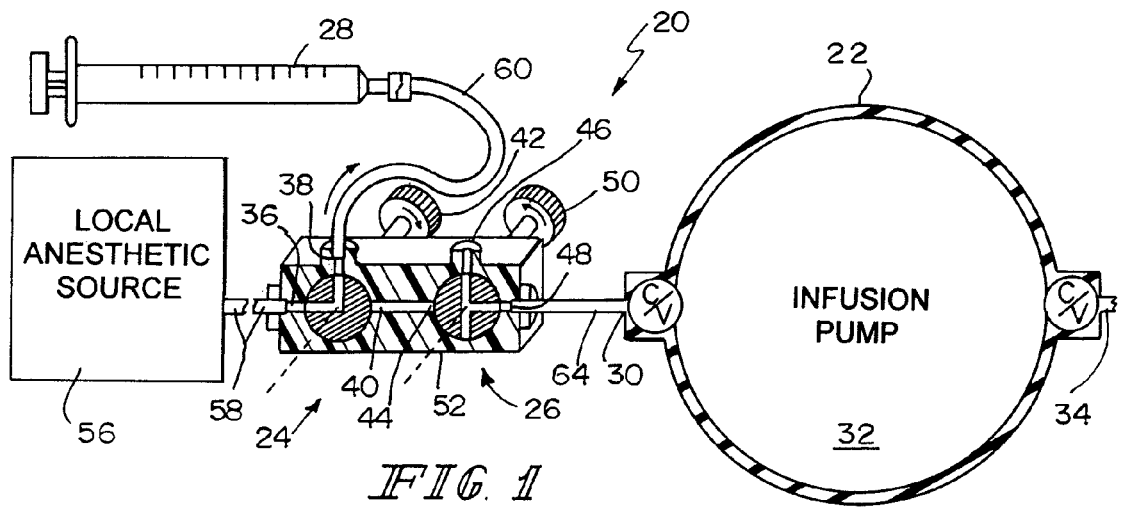
FIG. 1 illustrates a set of components assembled in accordance with the present invention in a first orientation useful in understanding the invention.

Turning now to the drawings, a kit 20 for charging an infusion pump 22 with a local anesthetic to be dispensed includes a first stopcock 24, a second stopcock 26 and a syringe 28. The pump 22 has an input port 30 through which the reservoir 32 of pump 22 is filled and an output port 34 through which local anesthetic in the reservoir 32 is pumped from the pump 22. Typical pumps 22 include the I-Flow Corporation ON-Q PainBuster pump, the Stryker Corporation PainPump®2 pump, and the like. An example of such a syringe 28 is a Beckton, Dickinson 60 ml syringe with luer lock tip.

The first stopcock 24 has an input port 36, a first input/output port 38 and a second output port 40. A manual control 42 is manipulable for selectively coupling either the first input/output port 38 or the second output port 40 to the input port 36. The second stopcock 26 has an input port 44 and first and second output ports 46, 48, respectively. A manual control 50 is manipulable for selectively coupling either the first output port 46 or the second output port 48 to the input port 44. The second output port 40 of the first stopcock 24 is adapted for coupling to the input port 44 of the second stopcock 26. In an illustrative embodiment, the first and second stopcocks 24, 26 are provided in a common body 52. An example of such a dual stopcock arrangement is the Argon Medical Devices, Inc., 041220001A double four way stopcock with male luer lock.

In a typical use, a source 56, such as a 100-200 ml bottle, of local anesthetic, such as ropivicaine, is hung and tapped or spiked with a length of tubing 58, such as a length of vented IV tubing with a drip chamber. An example of a kit for making this connection is the Abbott Laboratories Lifeshield® no. 11961 primary I. V. set with convertible pin, 100 inch (about 2.5 m) with backcheck valve and two CLAVE® ports. The free end of tubing 58 is coupled to port 36 of stopcock 24. A short length of tubing 60 is coupled at one end to port 38 of stopcock 24. Syringe 28 is coupled to the free end of length of tubing 60. Port 40 of stopcock 26 is coupled either through a length of tubing (not shown) or, where stopcocks 24, 26 are provided in a common body 52, through the common body 52, to port 44 of stopcock 26. Port 46 of stopcock 26 is vented to atmosphere. Port 48 of stopcock 26 is coupled through a length of tubing 64 to input port 30 of pump 22. An example of such a length of tubing is the Hospira, Inc., 3229-03, 30 inch (about 76 cm) extension set with Option-Lok®.

Figure 2:
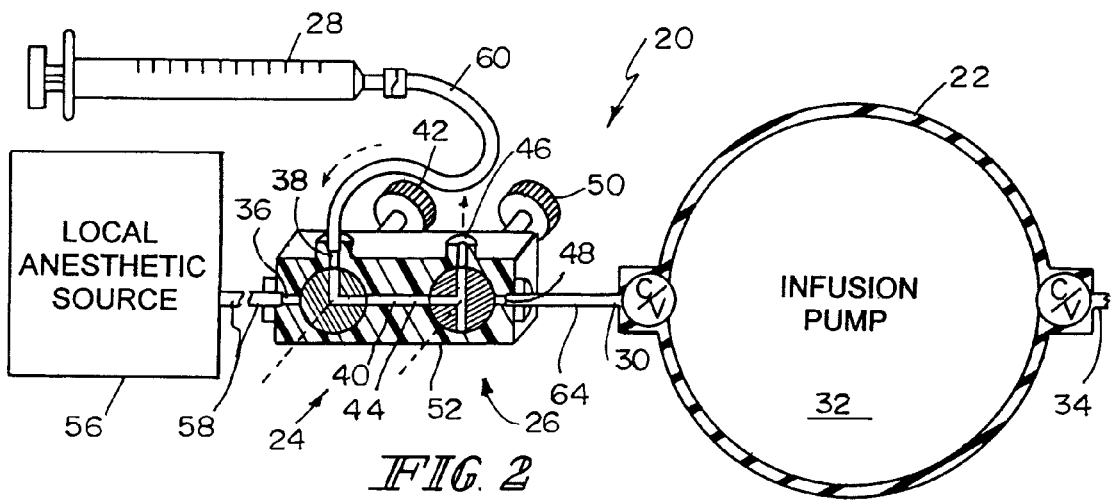
FIG. 2 illustrates a set of components assembled in accordance with the present invention in a second orientation useful in understanding the invention; and, FIG. 3 illustrates a set of components assembled in accordance with the present invention in a third orientation useful in understanding the invention.
Figure 3:
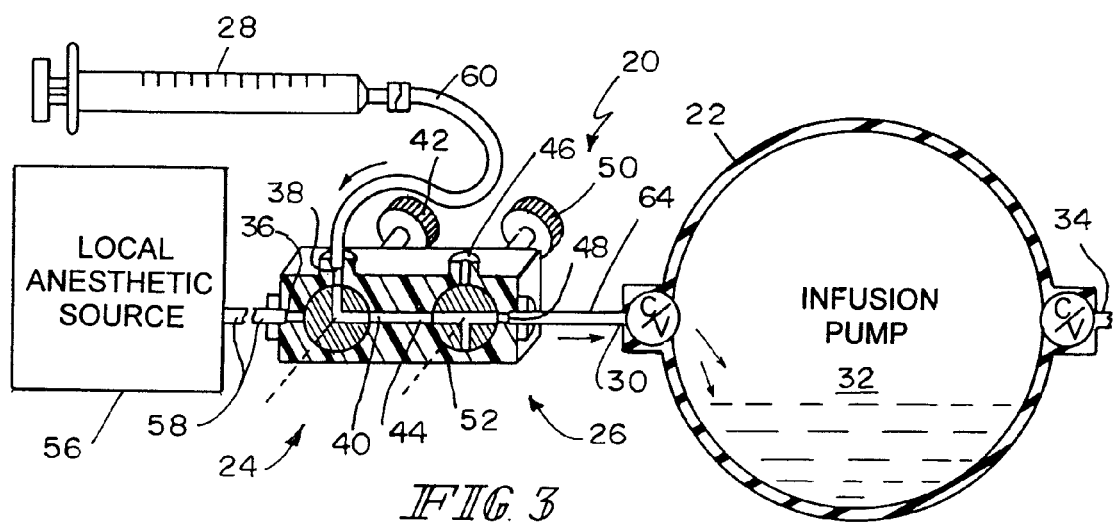

Now the user is ready to charge pump 22. The stopcocks 24, 26 are first placed in the orientations illustrated in FIG. 1, coupling the source 56 to syringe 28. The anesthetic is aspirated from source 56 into syringe 28. Any air drawn into syringe 28 is then pumped out by placing stopcocks in the orientations illustrated in FIG. 2, holding the syringe 26 below body 52 with its port up and pushing the plunger of syringe 26 to expel the air through port 46 to atmosphere. When the air has been expelled, the stopcocks 24, 26 are placed in the orientations illustrated in FIG. 3, and the plunger of syringe 26 is pushed, transferring the anesthetic from the body of syringe 28 to the reservoir 32 of pump 22. This process is repeated as often as necessary to transfer the desired amount of anesthetic to reservoir 32. As this is being done, the system remains relatively closed, reducing the likelihood of introduction of bacterial and viral agents and the like into the system. The output port of pump 22 is then coupled to the catheter which is to deliver the anesthetic into the surgical field, and the pump 22 is activated starting the flow of anesthetic to the field.

What is claimed is:

1. A kit for charging an infusion pump having a reservoir for holding a liquid which is to be dispensed by the pump, the pump having a pump input port through which the reservoir is filled and a pump output port through which liquid in the reservoir is pumped by the pump, the kit consisting of a dual stopcock having a dual stopcock input port, a dual stopcock input/output port, a dual stopcock first output port and a dual stopcock second output port, and first and second manual controls for controlling flow among the dual stopcock input port, the dual stopcock input/output port and the dual stopcock first and second output ports, wherein the dual stopcock input port, the dual stopcock input/output port, and dual stopcock first and second output ports are provided in a common body and the first and second manual controls are located on an exterior of the common body.

2. A kit for charging an infusion pump having a reservoir for holding a liquid which is to be dispensed by the pump, the pump having a pump input port through which the reservoir is filled and a pump output port through which liquid in the reservoir is pumped by the pump, the kit consisting of a dual stopcock having a dual stopcock input port, a dual stopcock input/output port, a dual stopcock first output port and a dual stopcock second output port, first and second manual controls for controlling flow among the dual stopcock input port, the dual stopcock input/output port and the dual stopcock first and second output ports, and a syringe adapted to be coupled to the dual stopcock input/output port, wherein the dual stopcock input port, the dual stopcock input/output port, and dual stopcock first and second output ports are provided in a common body and the first and second manual controls are located on an exterior of the common body.

3. A kit for charging an infusion pump having a reservoir for holding a liquid which is to be dispensed by the pump, the pump having a pump input port through which the reservoir is filled and a pump output port through which liquid in the reservoir is pumped by the pump, the kit consisting of a dual stopcock having a dual stopcock input port, a dual stopcock input/output port, a dual stopcock first output port and a dual stopcock second output port, first and second manual controls for controlling flow among the dual stopcock input port, the dual stopcock input/output port and the dual stopcock first and second output ports, a syringe adapted to be coupled to the dual stopcock input/output port, and tubing for coupling the dual stopcock input port to a source of the liquid, wherein the dual stopcock input port, dual stopcock input/output port, and dual stopcock first and second output ports are provided in a common body and the first and second manual controls are located on an exterior of the common body.

4. A kit for charging an infusion pump having a reservoir for holding a liquid which is to be dispensed by the pump, the pump having a pump input port through which the reservoir is filled and a pump output port through which liquid in the reservoir is pumped by the pump, the kit consisting of a dual stopcock having a dual stopcock input port, a dual stopcock input/output port, a dual stopcock first output port and a dual stopcock second output port, first and second manual controls for controlling flow among the dual stopcock input port, the dual stopcock input/output port and the dual stopcock first and second output ports, a syringe adapted to be coupled to the dual stopcock input/output port, tubing for coupling the dual stopcock input port to a source of the liquid, and tubing for coupling one of the dual stopcock first and second output ports to the pump input port, wherein the dual stopcock input port, dual stopcock input/output port, and dual stopcock first and second output ports are provided in a common body and the first and second manual controls are located on an exterior of the common body.

5. A kit for charging an infusion pump having a reservoir for holding a liquid which is to be dispensed by the pump, the pump having a pump input port through which the reservoir is filled and a pump output port through which liquid in the reservoir is pumped by the pump, the kit consisting of a first stopcock having a first stopcock input port, a first input/output port and a first stopcock second output port and a first manual control for selectively coupling either the first stopcock input port or the first stopcock second output port to the first input/output port, and a second stopcock having a second stopcock input port, a second stopcock first output port and a second stopcock second output port and a second manual control for selectively coupling either the second stopcock first output port or the second stopcock second output port to the second stopcock input port, the first stopcock second output port adapted for coupling to the second stopcock input port, wherein the first stopcock input port is configured to communicate only with the first stopcock first input/output port.

6. A kit for charging an infusion pump having a reservoir for holding a liquid which is to be dispensed by the pump, the pump having a pump input port through which the reservoir is filled and a pump output port through which liquid in the reservoir is pumped by the pump, the kit consisting of a first stopcock having a first stopcock input port, a first stopcock first input/output port and a first stopcock second output port and a first manual control for selectively coupling either the first stopcock input port or the first stopcock second output port to the first stopcock first input/output port, a second stopcock having a second stopcock input port, a second stopcock first output port and a second stopcock second output port and a second manual control for selectively coupling either the second stopcock first output port or the second stopcock second output port to the second stopcock input port, the first stopcock second output port adapted for coupling to the second stopcock input port, wherein the first stopcock input port is configured to communicate only with the first stopcock first input/output port, and a syringe adapted to be coupled to the first stopcock first input/output port.

7. A kit for charging an infusion pump having a reservoir for holding a liquid which is to be dispensed by the pump, the pump having a pump input port through which the reservoir is filled and a pump output port through which liquid in the reservoir is pumped by the pump, the kit consisting of a first stopcock having a first stopcock input port, a first stopcock first input/output port and a first stopcock second output port and a first manual control for selectively coupling either the first stopcock input port or the first stopcock second output port to the first stopcock first input/output port, a second stopcock having a second stopcock input port, a second stopcock first output port and a second stopcock second output port and a second manual control for selectively coupling either the second stopcock first output port or the second stopcock second output port to the second stopcock input port, the first stopcock second output port adapted for coupling to the second stopcock input port, wherein the first stopcock input port is configured to communicate only with the first stopcock first input/output port, a syringe adapted to be coupled to the first stopcock first input/output port, and tubing for coupling the first stopcock input port to a source of the liquid.

8. A kit for charging an infusion pump having a reservoir for holding a liquid which is to be dispensed by the pump, the pump having a pump input port through which the reservoir is filled and a pump output port through which liquid in the reservoir is pumped by the pump, the kit consisting of a first stopcock having a first stopcock input port, a first stopcock first input/output port and a first stopcock second output port and a first manual control for selectively coupling either the first stopcock input port or the first stopcock second output port to the first stopcock first input/output port, a second stopcock having a second stopcock input port, a second stopcock first output port, a second stopcock second output port and a second manual control for selectively coupling either the second stopcock first output port or the second stopcock second output port to the second stopcock input port, the first stopcock second output port adapted for coupling to the second stopcock input port, wherein the first stopcock input port is configured to communicate only with the first stopcock first input/output port, a syringe adapted to be coupled to the first stopcock first input/output port, first tubing for coupling the first stopcock input port to a source of the liquid, and second tubing for coupling the second stopcock second output port to the pump input port.

9. A kit for charging an infusion pump having a reservoir for holding a liquid which is to be dispensed by the pump, the pump having a pump input port through which the reservoir is filled and a pump output port through which liquid in the reservoir is pumped by the pump, the kit consisting of a first stopcock having a first stopcock input port, a first stopcock first input/output port, a first stopcock second output port and a first manual control for selectively coupling either the first stopcock input port or the first stopcock second output port to the first stopcock first input/output port, and a second stopcock having a second stopcock input port, a second stopcock first output port, a second stopcock second output port and a manual control for selectively coupling either the second stopcock first output port or the second stopcock second output port to the second stopcock input port, the first stopcock second output port adapted for coupling to the second stopcock input port, wherein the first stopcock input port is configured to communicate only with the first stopcock first input/output port, the first and second stopcocks being provided in a common body.

10. A kit for charging an infusion pump having a reservoir for holding a liquid which is to be dispensed by the pump, the pump having a pump input port through which the reservoir is filled and a pump output port through which liquid in the reservoir is pumped by the pump, the kit consisting of a first stopcock having a first stopcock input port, a first stopcock first input/output port, a first stopcock second output port and a first manual control for selectively coupling either the first stopcock input port or the first stopcock second output port to the first stopcock first input/output port, and a second stopcock having a second stopcock input port, a second stopcock first output port, a second stopcock second output port and a second manual control for selectively coupling either the second stopcock first output port or the second stopcock second output port to the second stopcock input port, the first stopcock second output port adapted for coupling to the second stopcock input port, wherein the first stopcock is configured to prevent communication between the first stopcock input port and the first stopcock second output port.

11. A kit for charging an infusion pump having a reservoir for holding a liquid which is to be dispensed by the pump, the pump having a pump input port through which the reservoir is filled and a pump output port through which liquid in the reservoir is pumped by the pump, the kit consisting of a first stopcock having a first stopcock input port, a first stopcock first input/output port, a first stopcock second output port and a first manual control for selectively coupling either the first stopcock input port or the first stopcock second output port to the first stopcock first input/output port, and a second stopcock having a second stopcock input port, a second stopcock first output port, a second stopcock second output port and a second manual control for selectively coupling either the second stopcock first output port or the second stopcock second output port to the second stopcock input port, the first stopcock second output port adapted for coupling to the second stopcock input port, wherein at least one of the second stopcock first output port and the second stopcock second output port is continuously in communication with the surrounding atmosphere.

* * * * *